US005731286A

United States Patent [19]

Harbeson et al.

[11] Patent Number: 5,731,286
[45] Date of Patent: Mar. 24, 1998

[54] CYCLIC NEUROKININ A ANTAGONISTS

[75] Inventors: Scott L. Harbeson; Stephen H. Buck, both of Cincinnati, Ohio

[73] Assignee: Merrell Pharmaceuticals, Inc., Cincinnati, Ohio

[21] Appl. No.: 811,913

[22] Filed: Mar. 5, 1997

Related U.S. Application Data

[63] Continuation of Ser. No. 638,405, Apr. 26, 1996, abandoned, which is a continuation of Ser. No. 497,142, Jun. 30, 1995, abandoned, which is a continuation of Ser. No. 277,945, Jul. 20, 1994, abandoned, which is a continuation of Ser. No. 953,325, Sep. 29, 1992, abandoned, which is a continuation of Ser. No. 852,353, Mar. 17, 1992, abandoned, which is a continuation of Ser. No. 392,236, Aug. 10, 1989, abandoned.

[51] Int. Cl.$^6$ ............................ A61K 38/12; C07K 5/00; C07K 7/00
[52] U.S. Cl. ............................... 514/11; 514/9; 514/17; 530/317; 530/329
[58] Field of Search ................... 514/11, 9, 17; 530/329, 317

[56] References Cited

U.S. PATENT DOCUMENTS

| 4,665,157 | 5/1987 | Wright | 530/328 |
|---|---|---|---|
| 4,742,156 | 5/1988 | Wright | 530/328 |
| 5,236,921 | 8/1993 | Emonds-Alt | 514/252 |
| 5,317,014 | 5/1994 | Fauchere | 514/17 |
| 5,317,020 | 5/1994 | Emonds-Alt | 514/255 |

FOREIGN PATENT DOCUMENTS

| 0284942 | 10/1988 | European Pat. Off. |
| B30428434 | 5/1991 | European Pat. Off. |
| 2216529 | 3/1989 | United Kingdom |

OTHER PUBLICATIONS

Sandberg, et al., Eur. Pept. Symp. 18th Symp., 369–372 (1984).
Sasaki, et al, "Soild Phase Synthesis of Peptides Containing the CH$_2$NH Peptide Bond Isostere," *Peptides*, 8, pp. 119–212, 1987.
Ploux, et al, "Interaction of tachykinins with their receptors studied with cyclic analogues of substance P and neurokinin B," Proc. Natl. Acad. Sci. USA, vol. 84, pp. 8095–8099, 1987.
Dutta, "Agonists and Antagonists of substance P," Drugs of the Future, vol. 12, (8) 1987.
Trends in Pharmacological Sciences, vol. 9, No. 1, pp. 1–3, 1988.
McKnight, A.T. et al., Regulatory Peptides 22, p. 127, (1988).
Williams, B.J. et al., Regulatory Peptides, 22, p. 189 (1988).
Coy, D.H. et al., *Journal of Biological Chemistry*, vol. 261, No. 11, pp. 5056–60, (1988).
*Trends in Pharmacological Sciences*, vol.9, No. 1, pp. 1–3, (1988).
Derwent 83–795699, Abstract DD 201024–A.
McKnight, A.T. et al., *Regulatory Peptides* 22, p. 127, (1988).
Williams, B.J. et al., Regulatory Peptides, 22, p. 189, (1988).
Rovero, et al., Peptides 10:593–595 (1989).
McKnight, et al., Reg. Peptides 22(1–2):126 (Jul. 1988).
McKnight, et al., Reg. Peptides 22(1–2):127 (Jul. 1988).
Williams, et al., Reg. Peptides 22(1–2):189 (Jul. 1988).
Fletcher, et al., Brit J of Pharm, Proceedings Supplement 90:266P (Mar. 1987).
McKnight, et al., Brit J of Pharm, Proceedings Supplement 91:360P (Jun. 1987).
Suman–Chauhan, et al., Brit J of Pharm. Proceedings Supp 95:747p (Dec. 1988).
Howarth, et al., Brit J of Pharm, Proceedings Supplement 96:360P (Mar. 1989).

*Primary Examiner*—Cecilia J. Tsang
*Assistant Examiner*—S. G. Marshall
*Attorney, Agent, or Firm*—T. Helen Payne

[57] ABSTRACT

Antagonists of neurokinin A which are derivatives of naturally occurring neurokinin A in which the amide bond connecting the two amino acids on the carboxy terminal end is modified are described. The antagonism is confirmed using conventional competitive binding and biochemical assays as well as conventional physiological tests and the use of these derivatives in a variety of conditions in which neurokinin A is implicated is also described.

9 Claims, 6 Drawing Sheets

CYCLIC NEUROKININ A ANTAGONISTS

CROSS-REFERENCE TO RELATED APPLICATION

This is a continuation of application Ser. No. 08/638,405 filed Apr. 26, 1996 abandoned, which is a continuation of application Ser. No. 08/497,142, filed Jun. 30, 1995, now abandoned; which is a continuation of application Ser. No. 08/277,945, filed Jul. 20, 1994, now abandoned, which is a continuation of application Ser. No. 07/953,325, filed Sep. 29, 1992, now abandoned; which is a continuation of application Ser. No. 07/852,353, filed Mar. 17, 1992, now abandoned; which is a continuation of application Ser. No. 07/392,236, filed Aug. 10, 1989, now abandoned, which is herein incorporated by reference.

FIELD OF THE INVENTION

This invention relates to cyclic peptide derivatives which are antagonists of neurokinin A.

BACKGROUND OF THE INVENTION

Substance P and related tachykinins, neurokinin A and neurokinin B, are a group of naturally occurring peptides shown to have wide distribution within body tissue and a wide variety of biological effects. While agonists and antagonists of substance P and neurokinin B are known and while agonists of neurokinin A are known as well, antagonists of neurokinin A have not yet been reported. Applicants have now discovered a class of neurokinin A antagonists. Such compounds are not only interesting from a biochemical viewpoint, but such compounds also have valuable pharmacological and medical utilities.

SUMMARY OF THE INVENTION

Cyclic peptide derivatives of the following structure 1 are antagonists of neurokinin A Formula 1 wherein $A_1$ is Gln, gln, His, his, Asn, asn or a group of the formula wherein

R" is a $C_1-C_5$ alkyl group substituted with an amino group;

$A_2$ is Trp, trp, Phe, phe, Tyr, tyr, Phg, phg, Cha, cha, Phe(4'-Cl), phe(4'-Cl), Npa, npa, Phe(4'-NO$_2$), or phe(4'-NO$_2$);

$A_3$ is Trp, trp, Phe, phe, Tyr, tyr, Phg, phg, Cha, cha, Phe(4'Cl), phe(4'-Cl), Npa, npa, Phe(4'-NO$_2$), phe(4'-NO$_2$), Val, or val;

$A_4$ is Gly, Ala, ala, or β-Ala;

B is a group of one of the formulae (a)

(b) —S—CH$_2$—,
(c) —O—CH$_2$—,
(d) —CH=CH—, (e)

(f) —CH$_2$—CH(OH)—, and (g)

and wherein

R is a hydrogen atom or an alkyl group of from 1 to 4 carbon atoms or is a phenylalkylene group wherein the alkylene moiety is straight or branched and has from 1 to 6 carbon atoms and wherein the phenyl moiety is unsubstituted or is mono substituted with a $C_{1-4}$ alkyl, $C_{1-4}$ alkoxy, hydroxy, or halogen group;

$R_1$ and $R_2$ are each independently selected from isopropyl, isobutyl, sec-butyl, n-butyl, and 2-(methylthio)ethyl groups or a pharmaceutically acceptable salt thereof. These novel cyclic peptide derivatives are antagonists of neurokinin A and are thus useful antiasthma, antiinflammatory, and antiarthrithic agents.

BRIEF DESCRIPTION OF THE DRAWING

——•—— NKA
——▲—— Cyclo(Gln—Trp—Phe—Gly—Leu—CH$_2$NH—Leu)
——☐—— Cyclo(Gln—Trp—Phe—Gly—Leu—CH$_2$NCH$_3$—Leu)

Figure 2

Figure 3

FIGS. 4 and 5 illustrate a comparison of the abilities of cyclo(Gln-Trp-Phe-Gly-Leu-CH₂NH-Leu) and cyclo(Gln-Trp-Phe-Gly-Leu-CH₂NCH₃-Leu) to antagonize the receptor-mediated, NKA-indiced PI turnover in hamster urinary bladder (Example 2). The abscissa (x-axis) logarithmically indicates the concentration of NKA. The ordinate (y-axis) indicates the observed PI turnover as a percentage of control. Values are MEAN ±S.E.M. from one experiment in triplicate. Identity of each dose-response line is as listed in the Figures. Both peptides at 100 nM (FIG. 4) and at 1 μM (FIG. 5) produced a parallel, rightward shift of the NA dose-response line. At each of the antagonist concentrations, both peptides were equipotent to each other.

Figure 4

Figure 5

FIG. 6. When NKA (10 μg) was applied directly onto the dome of the exposed bladder in anesthetized rats, it produced a sustained tonic contraction and an increase in frequency. When a second identical application was made 5 min after application of cyclo(Gln-Trp-Phe-Gly-Leu-CH₂NCH₃-Leu) (25 μg), the effects of NKA were markedly attenuated or completely blocked in two different rats. Continuous tracing shown for each animal. Methodology as described in Example 3.

DETAILED DESCRIPTION OF THE INVENTION

The following common abbreviations of the amino acids and amino and carboxy terminal groups are used throughout this specification:

Gly (or G)—glycine
Ala (or A)—alanine
Val (or V)—valine
Leu (or L)—leucine
Ile (or I)—isoleucine
Fum—fumaryl
Orn—ornithine
Pro (or P)—proline
Phe (or F)—phenylalanine
Trp (or W)—tryptophan
Met (or M)—methionine
Ser (or S)—serine
Thr (or T)—threonine
Cys (or C)—cysteine
Tyr (or Y)—tyrosine
Asn (or N)—asparagine
Gln (or Q)—glutamine
Asp (or D)—aspartic acid
Glu (or E)—glutamic acid
Lys (or K)—lysine
Arg (or R)—arginine
His (or H)—histidine
Nle—norleucine
Hyp—hydroxyproline
Cha—cyclohexylalanine
Glt—glutaryl
Mal—maleyl
β-Ala—β-Alanine
Npa—β-(2-naphthyl)alanine
3,4-dehydroPro—3,4-dehydroproline
Phg—phenylglycine
NMePgl—N-methyl-phenylglycine
Sar—sarcosine (N-methylglycine)
pSubPhe—para substituted phenylalanine
SubPhe—ortho, meta, or para, mono- or di-substituted phenylalanine
Ac—acetyl
Suc—succinyl
Phe(4'-Cl)—para-chloro-phenylalanine
Phe(4'-NO₂)—para-nitro-phenylalanine
NMeVal—N-methyl-valine In each instance a three letter code for an amino acid wherein the first letter is upper case signifies the amino acid is of the L-configuration. In a like manner, if the first letter of a three letter code for an amino acid is lower case, the amino acid is of the D-configuration.

An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. The alkylene moiety of the phenyl-alkylene groups of this invention can contain from 1 to 4 carbon atoms and may be straight or branched, for example, methylene, ethylene, propylene, butylene, isopropylidene, and sec-butylidene. The phenyl moiety of the phenylalkylene groups of this invention can be unsubstituted or can be mono substituted at the ortho, meta, or preferably the para positions. Unsubstituted phenyl or para hydroxyphenyl are preferred. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo, or iodo group.

The compounds of this invention wherein B is a have the structural formula 1a.

The compounds of this invention wherein B is a —S—CH$_2$— group have structural formula 1b.

The compounds of this invention wherein B is a —O—CH$_2$— group have structural formula 1c.

The compounds of this invention wherein B is a —CH=CH— group have structural formula 1d.

The compounds of this invention wherein B is a —CH$_2$—C(O)— group have structural formula 1e.

The compounds of this invention wheren B is a —CH$_2$CH(OH) group have structural formula 1f.

The compounds of this invention wherein B is a —C(O)NH— group have structural formula 1g.

It should be apparent that the cyclic peptide derivatives of this invention involve peptides wherein the normal peptide amide bond of the two carbon terminal amino acids of naturally occurring neurokinin A have been modified and linked via cyclization to the A$_1$ amino acid residue. Utilizing conventional nomenclature employed by peptide chemists, those compounds of formula 1 wherein R$_1$ and R$_2$ are each a sec-butyl group and B is an —NHCH$_2$— group (i.e., those compounds wherein the moiety connecting the A$_4$ residue to the A$_1$ residue is comprised of two Leu residues linked by a reduced amide bond) can be designated as LeuΨ[CH$_2$NH] Leu. This designation indicates that the amide carbonyl group of the penultimate Leu is reduced to a methylene group. Other nomenclature designations used to describe the peptide derivatives of this invention are Ψ[CH$_2$S], Ψ[CH$_2$O], Ψ[CH=CH], Ψ[C(O)CH$_2$], Ψ[CH(OH)CH$_2$], and Ψ[NHC(O)].

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, β-alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenyl-butyric acid (Pba), phenylalanines substituted at the ortho, meta, or paraposition of the phenyl moiety with one or two of the following, a (C$_1$–C$_4$) alkyl, (C$_1$–C$_4$) alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl) alanine, β-(1- and 2-naphthyl)alanine, O-alkylated derivatives of serine, threonine, or tyrosine, S-alkylated cysteine, the O-sulfate ester of tyrosine, 3,5-diiodotyrosine and the D-isomers of the naturally occurring amino acids.

The natural amino acids, with the exception of glycine and β-alanine, contain a chiral carbon atom. Unless otherwise specifically indicated, the optically active amino acids, referred to herein, are of the L-configuration. As is customary, the structure of peptides written out herein is such that the amino terminal end is on the left side of the chain and the carboxy terminal end is on the right side of the chain.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid.

As with any generic group of compounds certain groups are preferred. Applicants prefer those peptide derivatives of formula 1 wherein A$_1$ is a Gln, gln, Asn, or asn; those peptide derivatives wherein A$_2$ and A$_3$ are each a Trp, trp, Phe, phe, Tyr, tyr, Cha, cha, Phg, or phg; and those peptide derivatives wherein A$_4$ is a Gly, Ala, or ala. More preferred are those peptide derivatives wherein A$_1$ is Gln, A$_2$ and A$_3$ are each Trp or Phe, and wherein A$_4$ is Gly.

The peptides of this invention can be prepared by a variety of procedures readily known to those skilled in the art. Such procedures include the solid phase sequential procedure which can be performed using established automated methods such as by use of an automated peptide synthesizer. To prepare the peptide derivatives of this invention, resin bound amino acid corresponding to $A_4$ is used to sequentially add the amino acids corresponding to $A_3, A_2, A_1$, and finally that amino acid corresponding to $NH_2CHR_2CO_2H$. Subsequently, the modified "B" amide linkage is formed by adding the amino acid corresponding to $NH_2CHR_1CO_2H$, removal from the resin and cyclization. Procedures to be employed to prepare each of the modified peptide linkages are well known in the art and can be readily performed by skilled peptide chemists. The procedure to prepare those peptide derivatives of formula 1 wherein B is a —NHCO— group, that is the Ψ[NHCO] compounds, is known from Chorev and Goodman, Int. J. Pept. Protein Res., 21(3), 258–68 (1983). The procedure to prepare those peptide derivatives of formula 1 wherein B is a —COCH$_2$— or —CH(OH)CH$_2$— group, that is the Ψ[COCH$_2$] and Ψ[CH(OH)CH$_2$] compounds, respectively, is known from Holladay and Rich, Tetrahedron Letters, 24(41), 4401–04, (1983). The procedure to prepare those peptide derivatives of formula 1 wherein B is a —CH$_2$NH— group, that is the Ψ[CH$_2$NH] compounds, is known from Sasaki and Coy, Peptides, Vol. 8, pp. 119–121, 1987 and is more fully described below. The procedure to prepare those peptide derivatives of formula 1 wherein B is a —CH$_2$S— group, that is the Ψ[CH$_2$S] compounds, is known from Spatola and Darlak, Tetrahedron Letters, 44(3), 821–33 (1988). The procedure to prepare those peptide derivatives of formula 1 wherein B is a —CH$_2$O— group, that is the Ψ[CH$_2$O] compounds, is known from TenBrink, J. Org. Chem., 1987, 52, 418–22.

Subsequent to removal of the linear peptide from the resin and removal of any protecting groups as desirable, the linear peptide is cyclized using conventional procedures such as by treatment with triethylamine and diphenylphosphorylazide in dimethylformamide. Prior to purification of the crude cyclic peptide in the usual manner such as by use of chromatography, any remaining protecting and functional group precursors are removed or transformed into the desired group.

Specifically, the compounds of this invention wherein B is a —CH$_2$N(R)— group are prepared by reducing the N-methoxy-N-methylamide of formula 3 to produce the aldehyde of formula 4. The reduction can be performed in any way generally known and readily performed by those skilled in the art such as by use of lithium aluminum hydride (LAH). This reduction can be conveniently carried out by adding about one molar equivalent of LAH to a cooled, typically about 0° C., solution of a formula 3 compound in a nonreactive solvent such as an ethereal solvent such as tetrahydrofuran (THF) or diethylether. After the reaction is substantially complete, typically after about 30 minutes, the reaction mixture is quenched by the addition of, for example, 10% potassium or sodium hydrogen sulfate and then water. The product can then be isolated by, for example, extraction of the aqueous mixture with a solvent such as diethylether, washing the ether phase with cold, dilute aqueous hydrochloric acid, drying and solvent removal.

The formula 4 aldehyde is then reacted with a resin-bound peptide of formula 6 wherein R and $R_2$ are as defined for formula 1 and wherein Ⓡ represents the peptide resin. The initially formed Schiff base adduct is reduced in situ using, for example, sodium cyanoborohydride, to give a resin bound modified dipeptide of formula 7 wherein R, $R_1$ and $R_2$ are as defined for formula 1 and wherein Ⓡ represents the peptide resin.

The N-methoxy-N-methyl amides of formula 3 are prepared from the corresponding N-Boc protected acid in the usual manner. Carbonyldiimidazole is added to a dried solution of the N-Boc protected amino acid in an ethereal solvent such as diethylether. The reaction mixture is allowed to stir for from 10 minutes to 1 hour, typically for about 15–20 minutes. N,O-dimethyl-hydroxylamine HCl in DMF and a sterically hindered amine such as diisopropylethyl amine is added and the mixture allowed to stir for from about 6 hours up to about 24 hours at room temperature. The desired compound is then isolated by solvent evaporation and crude purification can be accomplished by, for example, flash flash chromatography on silica gel eluting with methylene chloride.

The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind. (London)* 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxy-methylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported-amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitro-phenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) keten-imines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxy-succinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in anhydrous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropyl-methoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The carboxylic hydroxyl group of Aspartic acid and Glutamic acid can be protected with a benzyl or cyclohexyl group. The preferred protecting group is benzyl.

These groups can be removed by procedures well known in the art. Typically protecting group removal is done after the peptide chain synthesis is complete but the protecting groups can be removed at any other appropriate time.

The ability of the peptide derivatives of formula 1 to act as antagonists of neurokinin A can be demonstrated by the ability of such peptides to compete with iodinated neurokinin A for mammalian neurokinin A (NK$_2$) receptors using the method of Buck, et al., *Science* 226: 987–989, 1984, and by the ability of such compounds to stimulate or to inhibit neurokinin A-induced phosphatidylinositol turnover using the method of Bristow, et al., *British J. Pharmacol.* 90: 211–21, 1987.

By virtue of the ability of the peptide derivatives of this invention to act as antagonists of neurokinin A, the compounds are useful as immunosuppressants and in the treatment of arthritis, asthma, pain, inflammation, tumor growth, gastrointestinal hypermotility, Huntington's disease, psychosis, neuritis, neuralgia, headache including migraine, hypertension, urinary incontinence, urticaria, carcinoid syndrome symptoms, influenza, and common cold. Effective doses, whether oral or parenteral, can be readily determined by those of ordinary skill in the art and are those doses which causes antagonism of the neurokinin A (NK$_2$) receptor. For example, effective doses of the peptides of this invention could be from about 0.5 µg/kg to about 500 mg/kg of the patient body weight per day. The compounds are conveniently administered in unit dosage forms containing from about 1 mg to about 500 mg of the active compound and can be administered in from one to four or more unit dosage forms per day. The term "patient" used herein is taken to mean mammals such as primates, including humans, sheep, horses, cattle, pigs, dogs, cats, rats, and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Figure 1:
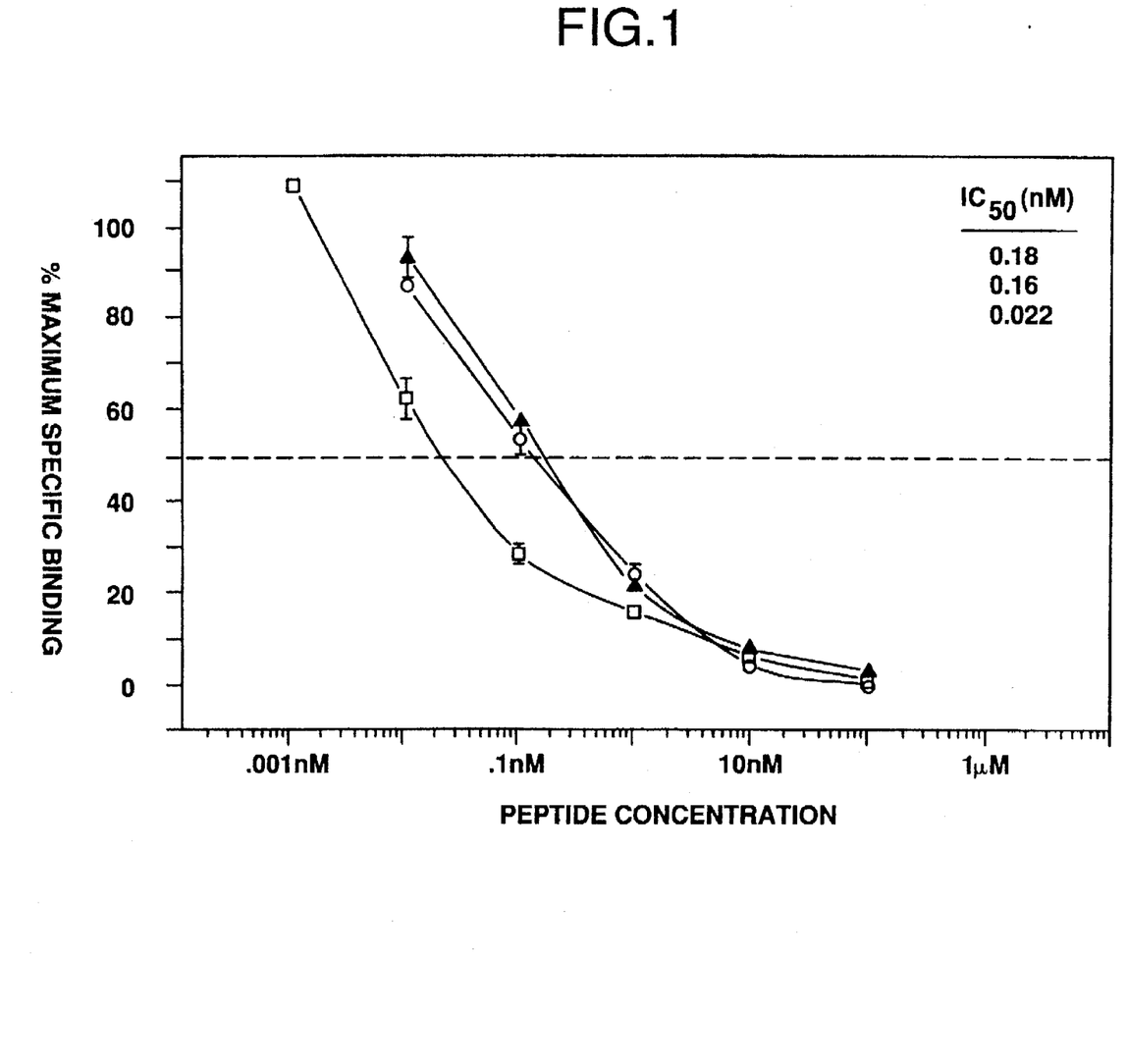
FIG. 1 illustrates the ability of cyclo(Gln-Trp-Phe-Gly-Leu-CH$_2$NH-Leu) and cyclo(Gln-Trp-Phe-Gly-Leu-CH$_2$NCH$_3$-Leu) to antagonize binding of agonist at the NKA receptor as demonstrated by the ability of test compound to compete for binding of I$_{125}$-labeled NKA from hamster urinary bladder (Example 1). The abscissa (x-axis) logarithmically indicates the concentration of agonist or antagonist of the neurokinin A (NKA) receptor. The ordinate (y-axis) indicates the observed specific binding for each tested agonist or antagonist measured as a percentage of maximum specific binding. Values are MEAN ±S.E.M. of 6–12 experiments. IC$_{50}$ values were estimated graphically from the 50% inhibition points and are listed in the Figure. Cyclo(Gln-Trp-Phe-Gly-Leu-CH$_2$NCH$_3$-Leu) was a more potent competitor than cyclo(Gln-Trp-Phe-Gly-Leu-CH$_2$NH-Leu) and was more potent than the agonist, NKA, itself.
Figure 2:
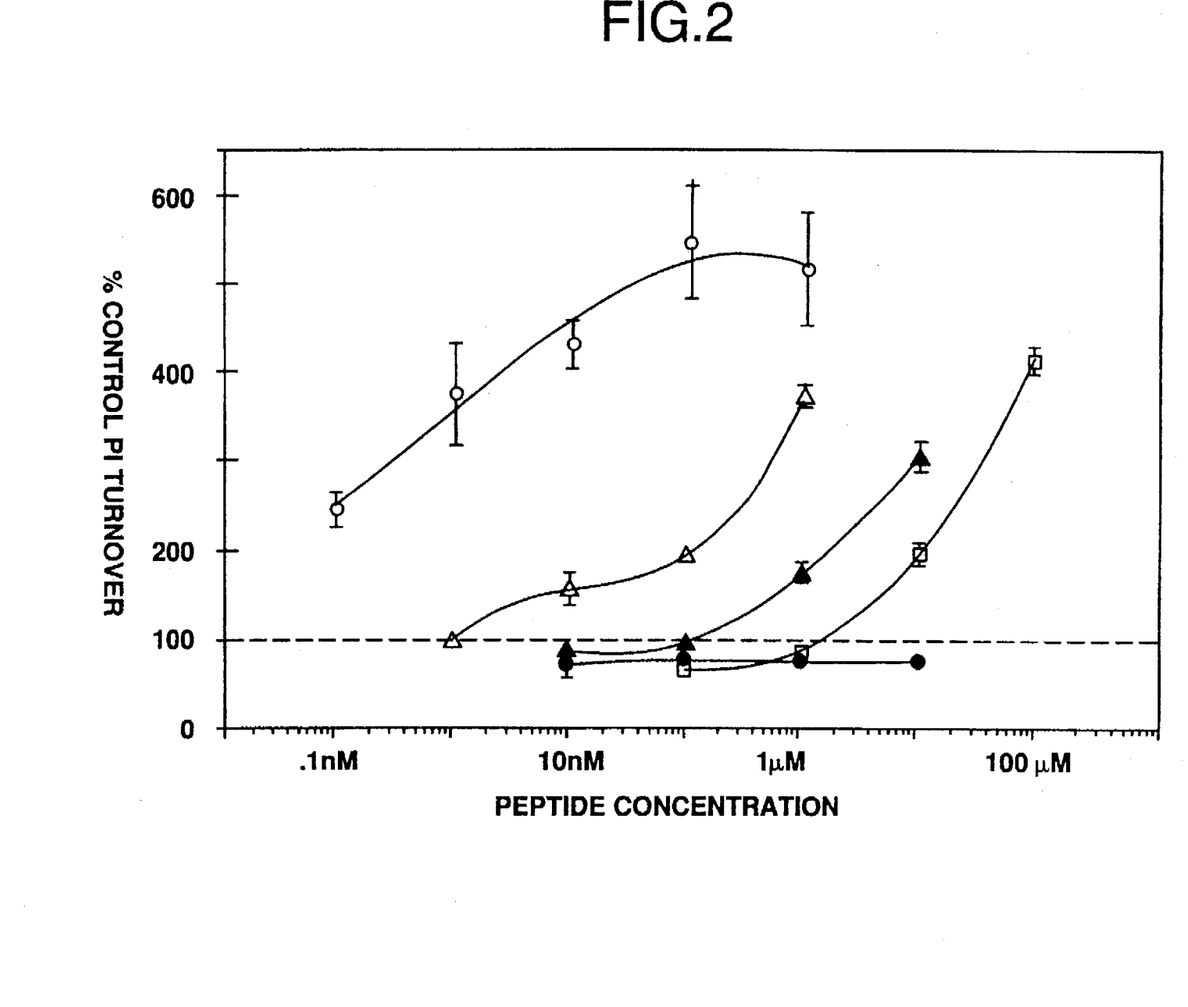
FIGS. 2 and 3 illustrate the ability of cyclo(Gln-Trp-Phe-Gly-Leu-CH$_2$NH-Leu) and cyclo(Gln-Trp-Phe-Gly-Leu-CH$_2$NCH$_3$-Leu), respectively, to produce a dose-related antagonism of the receptor-mediated, NKA-induced PI turnover in hamster urinary bladder (Example 2). The absicissa (x-axis) logarithmically indicates the concentration of agonist or antagonist of the NKA receptor. The ordinate (y-axis) indicates the observed PI turnover as a percentage of control. Values are MEAN ±S.E.M. from one experiment in triplicate. Identity of each dose-response line is as listed in the Figures. Cyclo(Gln-Trp-Phe-Gly-Leu-CH₂NH-Leu) (FIG. 2) at concentrations of 10 nM and 100 nM, and cyclo(Gln-Trp-Phe-Gly-Leu-CH₂NCH₃-Leu) (FIG. 3) at concentrations of 100 nM, 1 μM, and 10M produced a rightward shift of the NKA dose-response line. Neither compound alone at concentrations up to 10 μM produced any induction of PI turnover.
Figure 3:
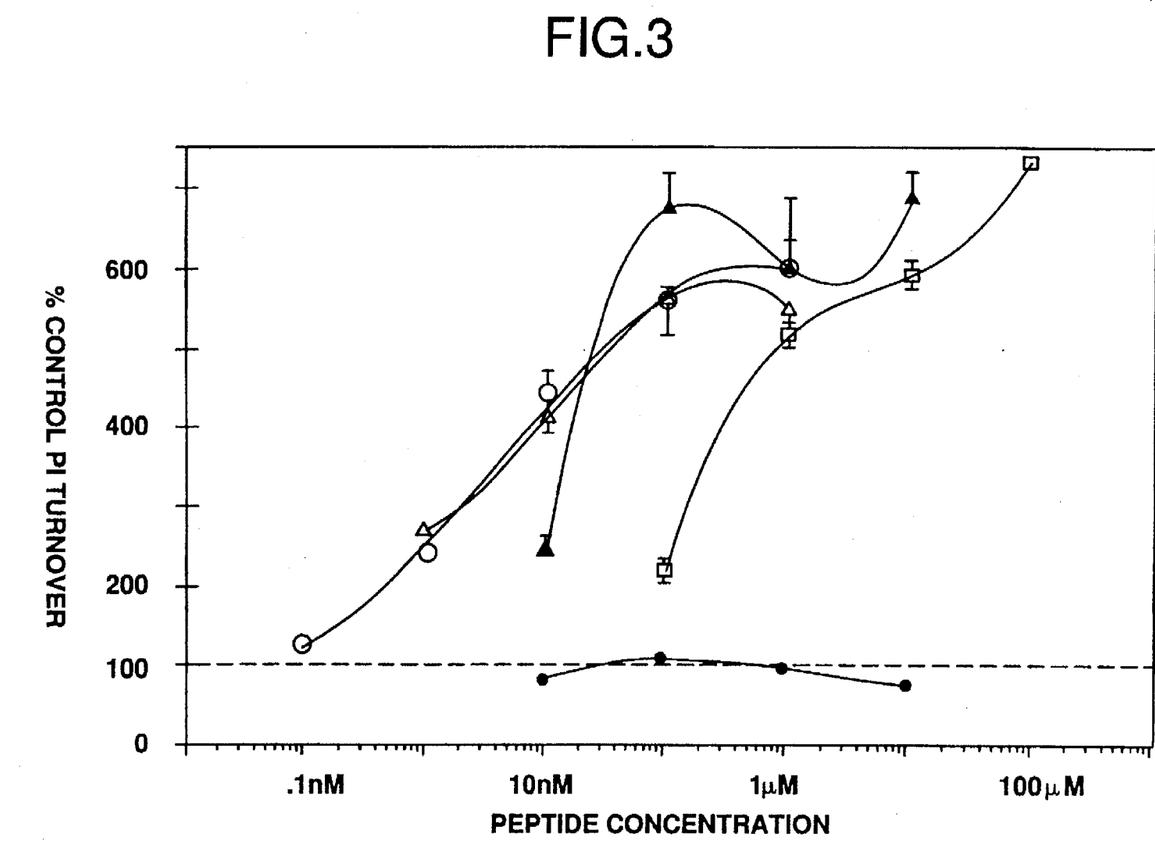
Figure 4:
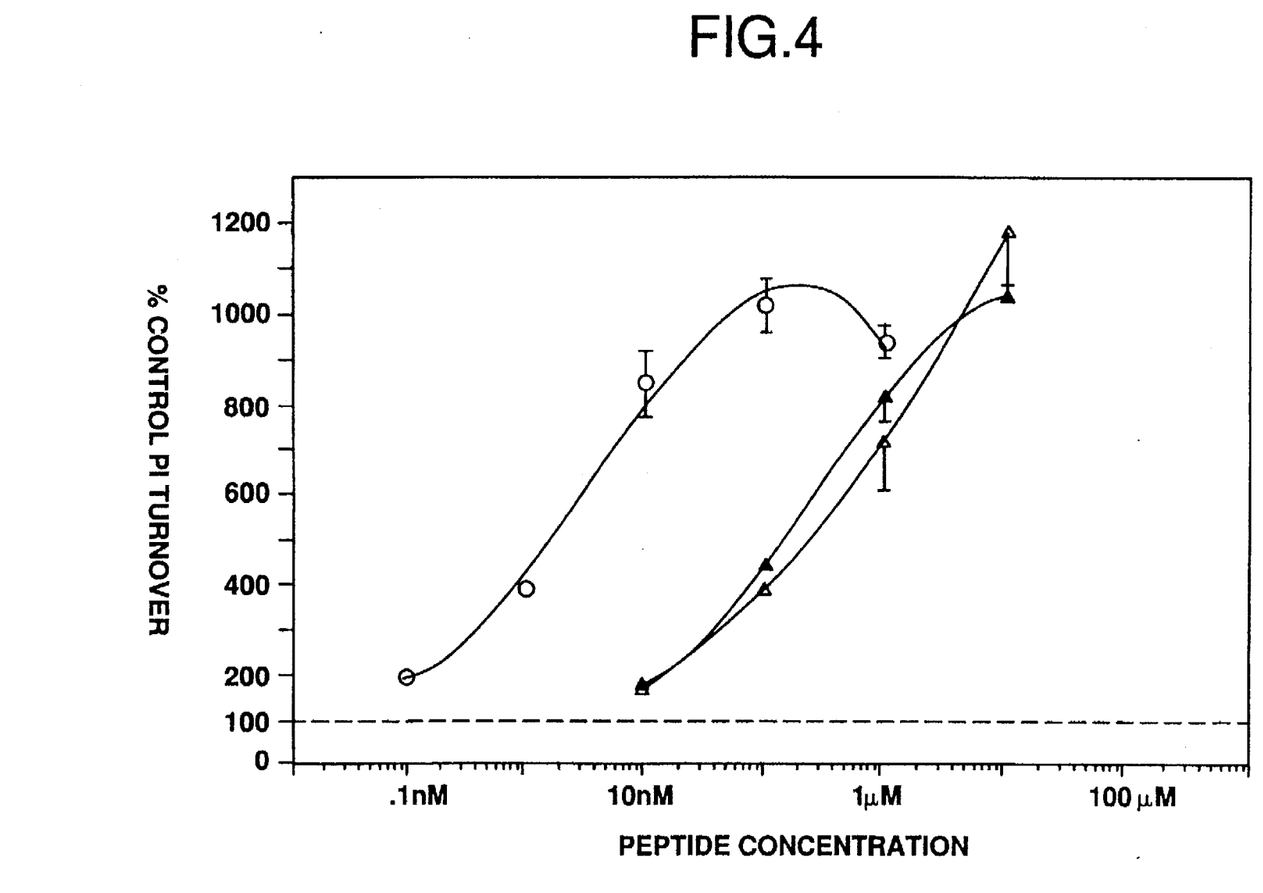
Figure 5:
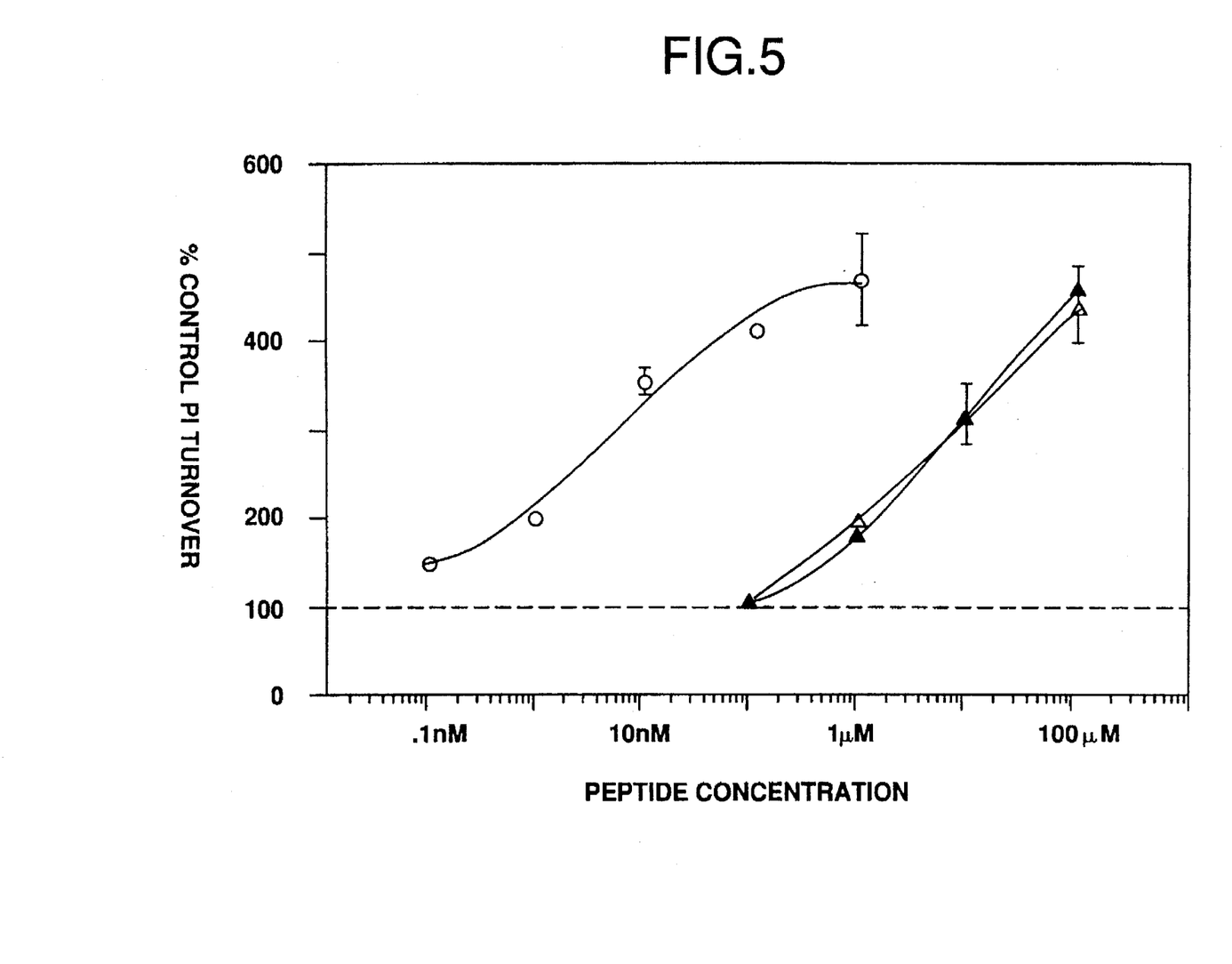

ANTAGONISM OF THE NEUROKININ A RECEPTOR BY CYCLIC GLN-TRP-PHE-GLY-LEUΨ[CH$_2$NH]LEU and CYCLIC GLN-TRP-PHE-GLY-LEUΨ[CH$_2$NCH$_3$]LEU AS DEMONSTRATED BY COMPETITION AT THE RECEPTOR FOR IODINATED NEUROKININ A Urinary bladders from several hamsters were pooled, minced, and homogenized in 50 mM TRIS-HCl (pH 7.4) containing 120 mM NaCl and 5 mM KCl at 4° C. and centrifuged at 48,000 X g for 15 minutes. The pellet was resuspended for 30 minutes in 50 mM TRIS-HCl (pH 7.4) containing 10 mM EDTA and 300 mM KCl at 4° C. The suspension was centrifuged as above and the pellet was washed two times in plain 50 mM TRIS-HCl (pH 7.4) and centrifuged similarly. The tissue was then resuspended in incubation buffer and an aliquot (approximately 3–5 mg tissue) was added to each assay tube to commence the assay. The assay tubes contained incubation buffer consisting of 50 mM TRIS-HCl (pH 7.4), 0.02% BSA, 40 µg/ml bacitracin, 4 µg/ml chymostatin, 4 µg/ml leupeptin, 2 mM MnCl$_2$, 0.1 nM $^{125}$iodohistidyl$^1$-neurokinin A (Amersham Corp.), and concentrations of the title compounds or standards ranging from 0.03 nM to 100 µM. The assay was allowed to proceed to equilibrium for 120 min at room temperature. After this time, the contents of each tube was rapidly filtered over Whatman GF/B filters presoaked in 0.5% BSA and the filters were rapidly washed two times with ice-cold plain 50 mM TRIS-HCl (pH 7.4). Filter-bound radioactivity was quantitated in a gamma counter. Specific binding (maximum) was defined as the difference between binding in the presence and absence of 1 µM unlabeled neurokinin A (NKA). Competition of iodinated NKA binding by test compounds or standards was expressed as a percentage of this maximum competition. IC$_{50}$ values (concentration required to inhibit 50% of receptor binding) were found to be 0.01–0.5 nM for the title compounds. (FIG. 1)

EXAMPLE 2

ANTAGONISM OF THE NEUROKININ A RECEPTOR BY CYCLIC GLN-TRP-PHE-GLY-LEUΨ[CH$_2$NH]LEU and CYCLIC GLN-TRP-PHE-GLY-LEUΨ[CH$_2$NCH$_3$]LEU AS DEMONSTRATED BY THE EFFECT ON PHOSPHATIDYLINOSITOL TURNOVER Urinary bladders from several hamsters were pooled and chopped at 350 µm with a tissue chopper. The chopped tissue was then incubated in 37° C. Krebs-Hepes buffer with fresh buffer changes every 15 minutes for 30 minutes. The tissue was then incubated in this buffer containing 100–200 µCi of $^3$H-inositol at 37° C. The tissue was then washed and incubated for another 30 minutes in Krebs-Hepes (containing 10 mM Li+) at 37° C. with fresh buffer change every 15 minutes. Portions of the tissue mass (approximately 10–20 mg per assay tube) were then placed in Li+ buffer, test compound was then added in 25 µl, and then various concentrations of NKA were added in 25 µl in a final volume of 250 µl. Test compound was evaluated at concentrations ranging from 1 nM to 100 µM and NKA concentrations ranged from 1 nM to 10 µM. Test compound was also evaluated alone at the indicated concentrations to test for agonist activity. After 30 minutes at room temperature, the phosphatidylinositol turnover was terminated by the addition of 940 µl chloroform:methanol (1:2), followed by 310 µl chloroform, followed by 310 µl water. Each tube was then vortexed for 15 seconds and then centrifuged at 3000 rpm for 10 minutes to separate the phases. 900 µl of the top (aqueous) phase was then loaded onto a 0.5 ml Biorad AG-1X8 (formate) ion exchange column. 50 µl of the bottom phase (chloroform) was withdrawn from each tube and placed in a counting vial, dried, and counted in scintillation fluid. The material on the columns was washed in order with:

1) 10 ml of water
2) 5 ml of 5 mM disodium tetraborate/60 mM sodium formate 3) 10 ml of 1M ammonium formate in 0.1M formic acid The final (third) wash was collected and one ml was mixed with 6 ml of ACS scintillant and counted. The ratio of these counts (total inositol phosphates) to the corresponding organic phase counts was then calculated for each sample. The ratios in the presence of test compound and/or standards were then compared to the ratios for control tubes (i.e., no stimulating agonist). Dose-response lines were constructed and the abilities of test compounds to stimulate or to inhibit neurokinin A-induced phosphatidylinositol turnover were determined by graphical analysis or with the aid of a computer program and are illustrated in FIGS. 2 THROUGH 5.

EXAMPLE 3

ANTAGONISM OF NEUROKININ A BY CYCLIC GLN-TRP-PHE-GLY-LEUΨ[CH$_2$NCH$_3$] LEU IN THE IN SITU RAT URINARY BLADDER PREPARATION

Figure 6:
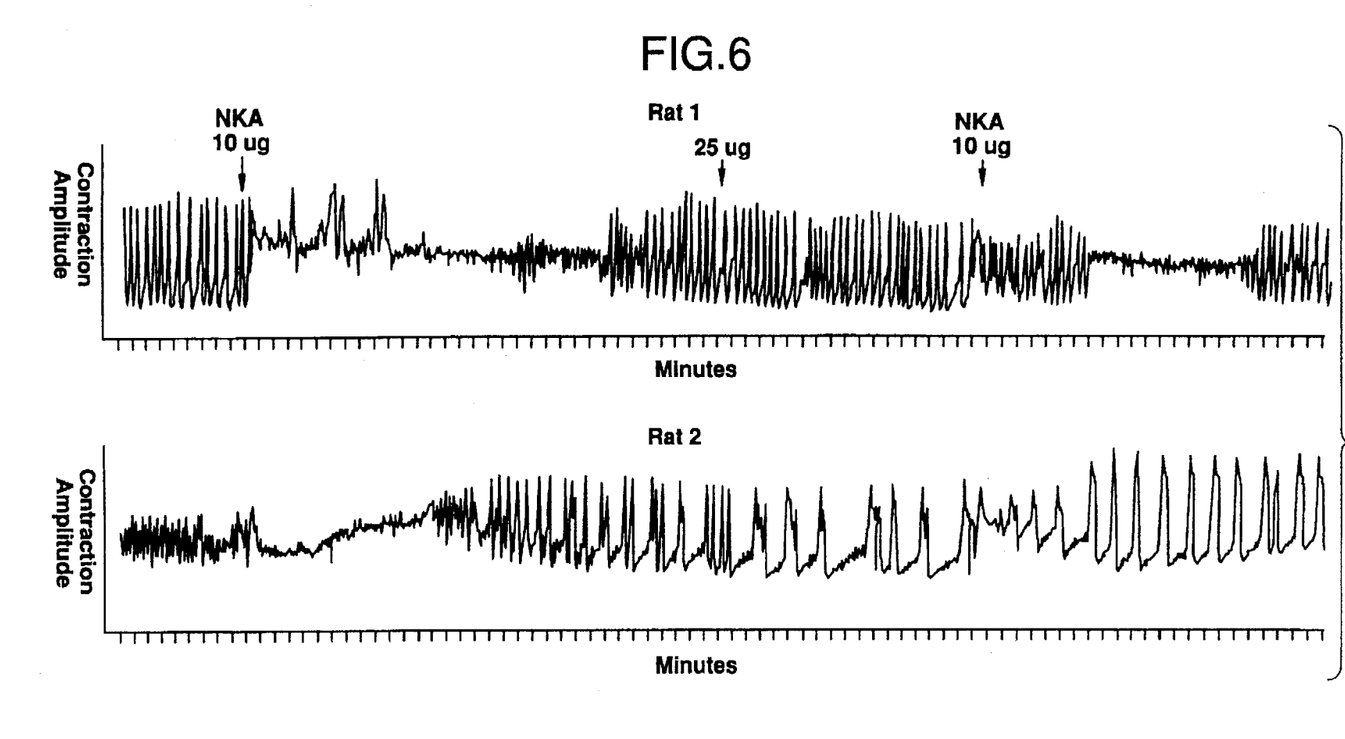

Rats, (female Sprague-Dawley, 150–200 g) were anesthetized with ketamine HCl (100 mg/kg i.p.) supplemented with urethane (1.2 g/kg i.p.). The bladder was exposed and evacuated according to the method of Dray (*J. Pharmacol. Methods* 13: 157–165, (1985)). A needle was inserted into the apex of the bladder dome and saline was perfused through the bladder at a rate of 100 μl per minute. Bladder outflow was collected via a polyethylene cannula inserted into the urethra. Bladder contractions were monitored through a flow pressure transducer connected in series with the perfusion system. Test compounds were applied onto the bladder dome in 40–100 μl of saline or saline containing a minimum of DMSO. The application vehicle containing up to 75% DMSO had no direct effect nor did it affect the contractions induced by subsequent NKA. The threshhold concentration of NKA for contraction was approximately 10 μg and this amount was used routinely. Antagonist was similarly applied onto the bladder 5 min before a repeated application of NKA. Repeated application of 10 μg NKA did not result in any tachyphylaxis. Amplitude (force) of contraction and 1-min time intervals were recorded continuously for each animal. Examples of tracings are shown in FIG. 6.

EXAMPLE 4

I. Boc-Leu-aldehyde synthesis (Fehrentz, J. A. and Castro, B. *Synthesis*, 1983, 676–678):

A. N-t-Boc-Leucine N-methoxy-N-methylamide:

15.0 mmoles of Boc-Leucine hydrate was dissolved in 30 ml dry ether. The solution was dried over anhydrous MgSO$_4$ and the solid removed by filtration. 16.5 mmoles of carbonyldi-imidazole was added to the filtrate and the reaction stirred 20 minutes at room temperature. To the resulting solution was added a suspension of 0,N-dimethylhydroxylamine hydrochloride (22.5 mmoles) in 15 ml dimethylformamide and 3.9 ml diiso-propylethylamine. The reaction mixture was stirred overnight at room temperature. The reaction was diluted into ethyl acetate (75 ml) and washed with cold 1N HCl (3×40 ml), saturated NaHCO$_3$ (3×40 ml) and saturated NaCl (1×40 ml). The organic phase was dried with MgSO$_4$, filtered and the ethyl acetate removed in vacuo.

Analytical Data: R$_f$ (silica gel F254): 0.51 (ethyl acetate/hexane 3/2); $^1$H-NMR (CDCl$_3$) (TMS int): δ=0.95 ppm (2d, 6H, J=6.6 Hz); 1.42 (s, 11H); 1.64–1.80 (m, 1H); 3.20 (s, 3H); 3.80 (s, 3H); 4.72 (m, 1H); 5.10 (d, 1H, J=7.5 Hz). Mass Spec: M+H$^+$: Theoretical: 275. Observed: 275.

B. Boc-Leucine aldehyde:

2.5 mmoles of Boc-leucine N-methoxy-N-methylamide were dissolved in dry ether (30 ml). To this solution was added 3.2 mmole of lithium aluminum hydride (1M solution in tetrahydrofuran). The reaction was stirred 20 minutes at room temperature and then carefully quenched by addition of a solution of NaHSO$_4$ (0.6 g) in 10 ml water. The reaction mixture was added to 75 ml ether and washed with cold 1N HCl (3×30 ml), saturated NaHCO$_3$ (3×30 ml) and saturated NaCl (1×30 ml). The organic phase was dried with MgSO$_4$, filtered and the solvent removed in vacuo.

Analytical Data: Rf (silica gel 60 F254): 0.68 (ethyl acetate/hexane 3/2). Mass Spec: M=H$^+$: Theoretical: 216. Observed: 216.

II. Synthesis of Leu-Gln-Trp(CHO)-Phe-Gly-PAM-Resin:

Standard solid phase peptide synthesis techniques on an automated peptide synthesizer were used beginning with Boc-Gly-PAM resin (0.5 mmol). The remaining amino acids were added sequentially (Phe, Trp(CHO), Gln, Leu). The Boc protecting group was then removed with trifluoroacetic acid, the resin was neutralized with diisopropylethylamine. The resin was then washed with dimethylformamide, dichloromethane and dried.

III. Formation of reduced amide bond (LeuΨ[CH$_2$NH] Leu):

The Boc-Leu aldehyde (2 mmoles) was dissolved in 1% acetic acid in dimethylformamide (10 ml) and this solution was added to the reaction vessel containing the peptide-resin (0.5 mmoles, see II. above). To this mixture was added a solution of NaCNBH$_3$ (150 mg) in 2 ml dimethylformamide. The mixture was shaken for 4 hours, the reaction vessel was drained and the resin washed with dimethylformamide, then dichloromethane.

IV. Synthesis of cyclo[LeuΨ[CH$_2$NH]Leu-Gln-Trp-Phe-Gly]::

The peptide was cleaved from the resin and globally deprotected using anhydrous HF/anisole (10:1). A portion of the crude peptide (77 mg) was cyclized by dissolving in dimethylformamide (15 ml) and then adding triethylamine (0.2 ml) and diphenylphosphonylazide (0.08 ml). After stirring at room temperature for 12 hours, the solvent was removed in vacuo. The Trp(CHO) residue was then deformylated by dissolving the crude cyclic peptide in 1:1 acetonitrile:water (v/v) (60 ml) and adding triethylamine (2.0 ml). The deformylation reaction was stirred 12 hours at room temperature and then the solvent was removed in vacuo. The crude cyclic peptide was purified using reverse phase HPLC techniques to provide the pure compound. Yield: 27.9 mg, 38.2 μmoles.

Analytical data: Amino Acid Analysis (HCl digest): Glx (0.83), Phe (0.97), Gly (1.03); Fast Atom Bombardment Mass Spectrometry: (M+H)$^+$; Theoretical, 731; Found, 731; Peptide Content: 50.7%.

V. Synthesis of cyclo[LeuΨ[CH$_2$NCH$_3$]Leu-Gln-Try-Phe-Gly]:

N-Methyl-Leu-Gln-Trp(CHO)-Phe-Gly-PAM resin (prepared using Boc-N-methyl Leucine according to II above) was reacted with 2.0 mmoles Boc-Leu aldehyde as described in III above. The peptide synthesis was then completed as described in IV above.

Analytical Data: Amino Acid Analysis: (HCl digest) Glx (0.72); Gly (1.04); Phe (0.96). Peptide Content: 63.7%. Fast Atom Bombardment Mass Spectrometry: M+H$^+$. Theoretical: 745. Observed: 745.

VI. Synthesis of cyclo[LeuΨ[CH$_2$NR]Leu-Gln-Trp-Phe-Gly]:

Boc-Leu [Ψ(CH$_2$NH)]-Leu-Gln-Trp(CHO)-Phe-Gly-PAM-resin is prepared according to steps II and III above. The resin is then reacted with 2.5 mmoles of R—CHO in 10 ml of 1% HOAc in dimethylformamide in the presence of NaCNBH$_3$ as described in III above. The synthesis of the peptide is then completed as described in IV above.

We claim:

1. A peptide of the formula

Formula 1 wherein;

A$_1$ is Gln;
A$_2$ is Trp;
A$_3$ is Phe;
A$_4$ is Gly;
B is a group of one of the formulae wherein;

R is a hydrogen atom or an alkyl group of from 1 to 4 carbon atoms; and

R$_1$ and R$_2$ are each independently selected from isopropyl, isobutyl, sec-butyl, n-butyl, and 2-(methylthio)ethyl groups;

or a pharmaceutically acceptable salt thereof.

2. A peptide of claim 1 wherein R is hydrogen.

3. A peptide of claim 1 wherein R is methyl.

4. A peptide of claim 1 where in R$_1$ is n-butyl.

5. A peptide of claim 1 where in R$_2$ is n-butyl or 2-methylthoethyl.

6. A peptide of claim 1 which is cyclic Gln-Trp-Phe-Gly-Leu[CH$_2$NCH$_3$]Leu.

7. A peptide of claim 1 which is cyclic Gln-Trp-Phe-Gly-Leu[CH$_2$NH]Leu.

8. A pharmaceutical composition comprising a compound of one of claims 1–6 and a pharmaceutically acceptable carrier.

9. A method of treating asthma in a patient in need thereof comprising administering an effective amount of a peptide of one of claims 1–7.

* * * * *